United States Patent [19]

Ford

[11] Patent Number: 4,836,908

[45] Date of Patent: Jun. 6, 1989

[54] MINIATURIZED REFERENCE ELECTRODES

[75] Inventor: Jayme R. Ford, Mount Prospect, Ill.

[73] Assignee: Abbott Laboratories, Abbott Park, Ill.

[21] Appl. No.: 136,886

[22] Filed: Dec. 22, 1987

[51] Int. Cl.[4] .................... G01N 27/28; G01N 27/30
[52] U.S. Cl. .................................... 204/435; 204/414
[58] Field of Search ................................ 204/414, 435

[56] References Cited

U.S. PATENT DOCUMENTS

| | | | |
|---|---|---|---|
| 3,449,232 | 6/1969 | Bailey | 204/435 |
| 3,926,764 | 12/1975 | Ruzicka et al. | 204/435 |
| 4,031,606 | 6/1977 | Szonntagh | 204/435 |
| 4,592,824 | 6/1986 | Smith et al. | 204/435 |

FOREIGN PATENT DOCUMENTS 1549044  7/1979  United Kingdom ............... 204/414

Primary Examiner—T. Tung
Attorney, Agent, or Firm—Robert W. Stevenson; Martin L. Katz

[57] ABSTRACT

A reference electrode is disclosed for use in potentiometric analysis of ion activity in a solution.

16 Claims, 5 Drawing Sheets

MINIATURIZED REFERENCE ELECTRODES

BACKGROUND OF THE INVENTION

This invention relates to reference electrodes for use in potentiometric measurements.

The art is replete with reference electrodes for potentiometric measurements. Reference electrodes provide a reference potential in electrochemical cells used for the measurement of ion activity. A reference electrode is typically used with an ion selective electrode to obtain a potentiometric signal relating to ion activity in a solution in which the two electrodes are introduced.

In addition to completing the electrical circuit, a reference electrode is supposed to provide a stable and unchanging reference potential.

Heretofore, commercial reference electrodes have typically been relatively expensive and large. Furthermore, many of them take a long time to stabilize when exposed to ionic solutions. While they can eventually provide fairly stable and unchanging reference potentials, many electrodes can take up to 20 minutes or longer to stabilize. This time period allows conventional electrodes to be affected by changes in pressure and temperature.

SUMMARY OF THE INVENTION

The present invention is a miniaturized reference electrode which can be constructed inexpensively, and can be disposed of even after a single use. Preferably, however, the same electrode can be used a number of times, over 200 times, in fact. The reference electrode of this invention also reaches equilibrium rapidly, typically less than twenty seconds, and is stable over a broad temperature and pressure range.

The reference electrode of this invention includes a silver-silver chloride chip and a housing having an internal cavity filled with electrolyte. The cavity has a first opening across which the chip is disposed, and a second opening spaced from the first opening. The ratio of the area of the first opening to the area of the second opening ranges from about 14.0 to about 728.0. In addition, the ratio of the distance between the first and second openings to the area of the first opening is about 2.0 $cm^{-1}$ to about 66.0 $cm^{-1}$. With these features and proportions, extremely small reference electrodes can be constructed wherein the area of the second opening ranges from about $8.00 \times 10^{-5}$ $cm^2$ to about $3.3 \times 10^{-4}$ $cm^2$. Such reference electrodes are extremely small and can be designed by varying the amount of silver-silver chloride matrix in the electrode to be disposable after a single use or after multiple uses.

DETAILED DESCRIPTION OF THE PREFERRED EMBODIMENT

Figure 1:
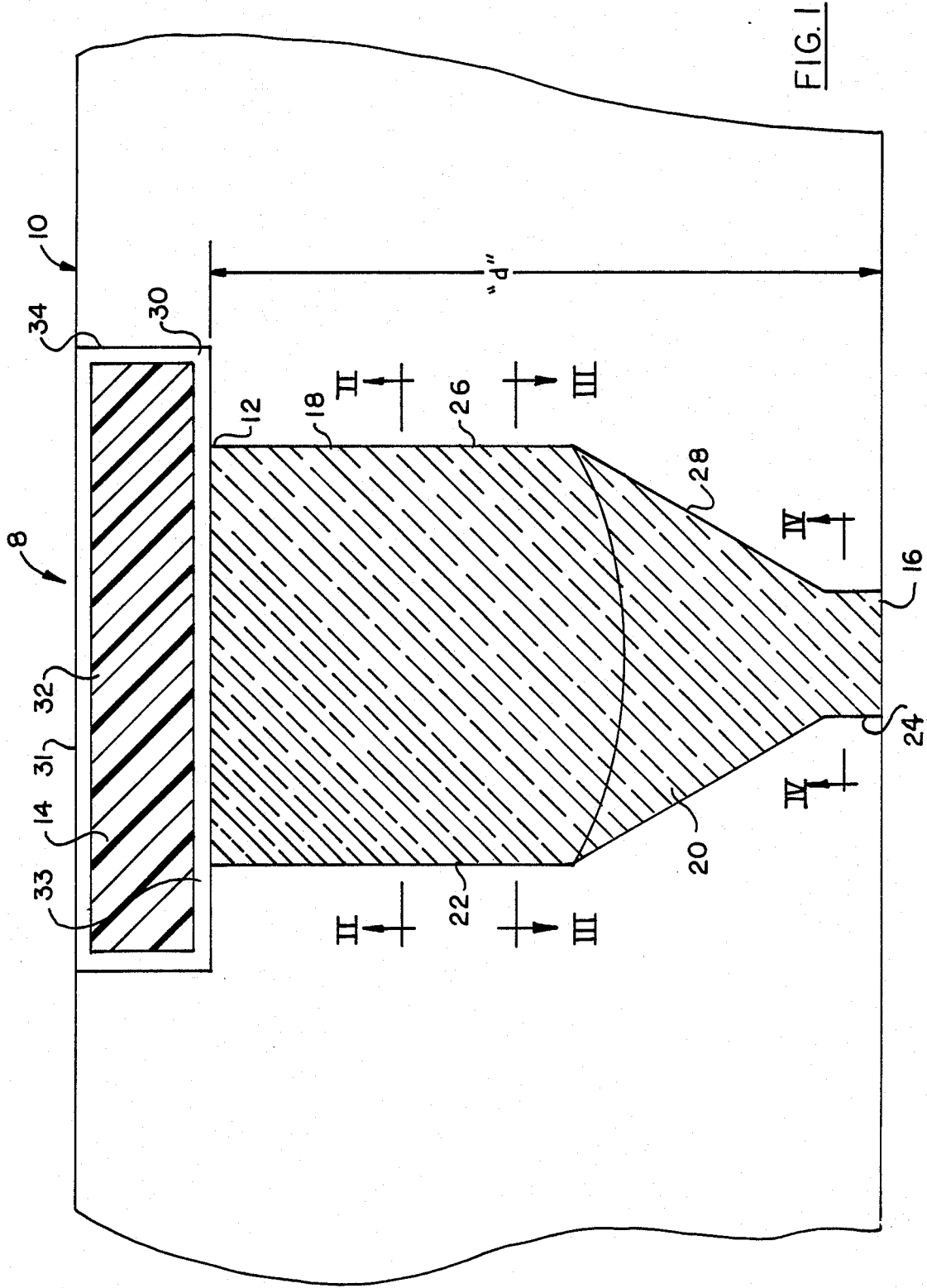
FIG. 1 is a cross-sectional view of the reference electrode of the present invention.

The reference electrode 8 of the present invention includes a housing 10 (FIG. 1). Housing 10 includes a first opening 12 across which a silver-silver chloride chip 14 is disposed. Housing 10 further includes a second opening 16 which will be exposed to the testing medium of interest. Between openings 12 and 16, housing 10 has an internal cavity 18 which is filled with electrolyte 20.

Figure 2:
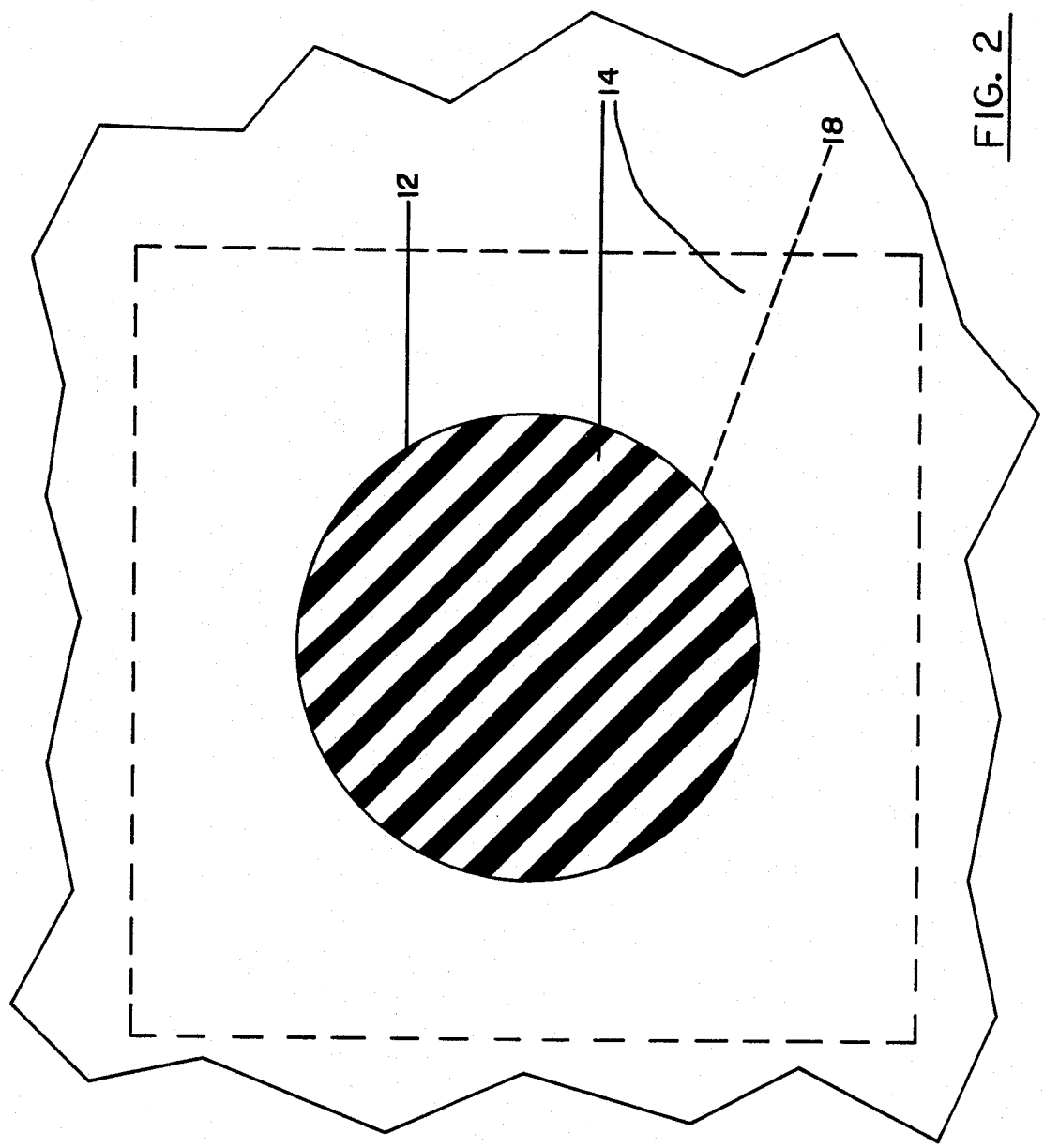
FIG. 2 is a cross-section along the plane of line II—II of FIG. 1.
Figure 3:
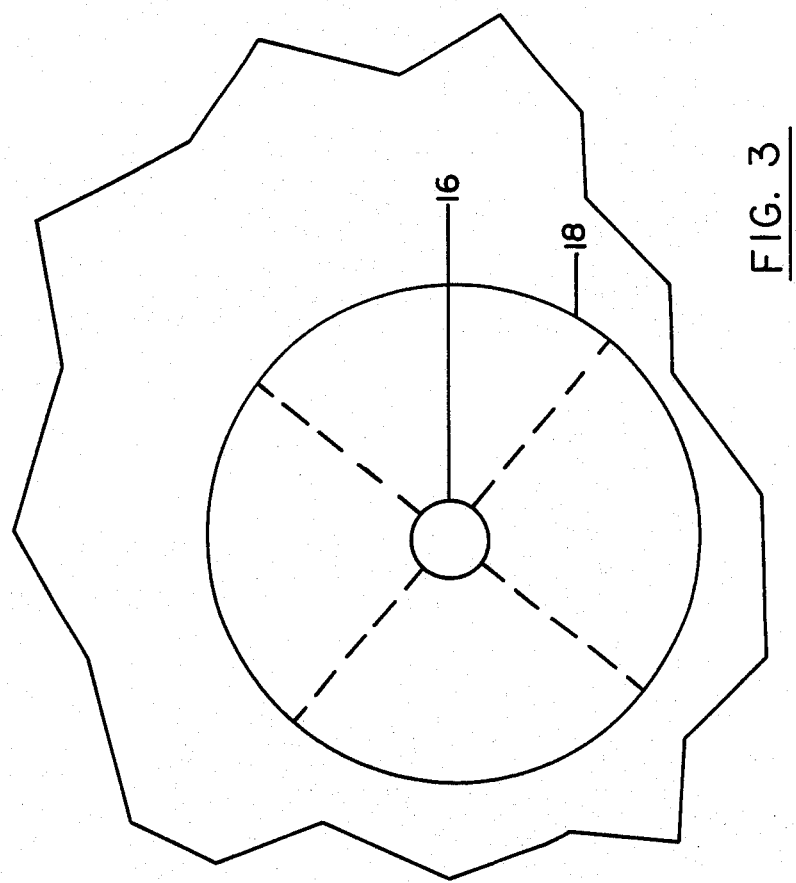
FIG. 3 is a cross-section along the plane of line III—III of FIG. 1.
Figure 4:
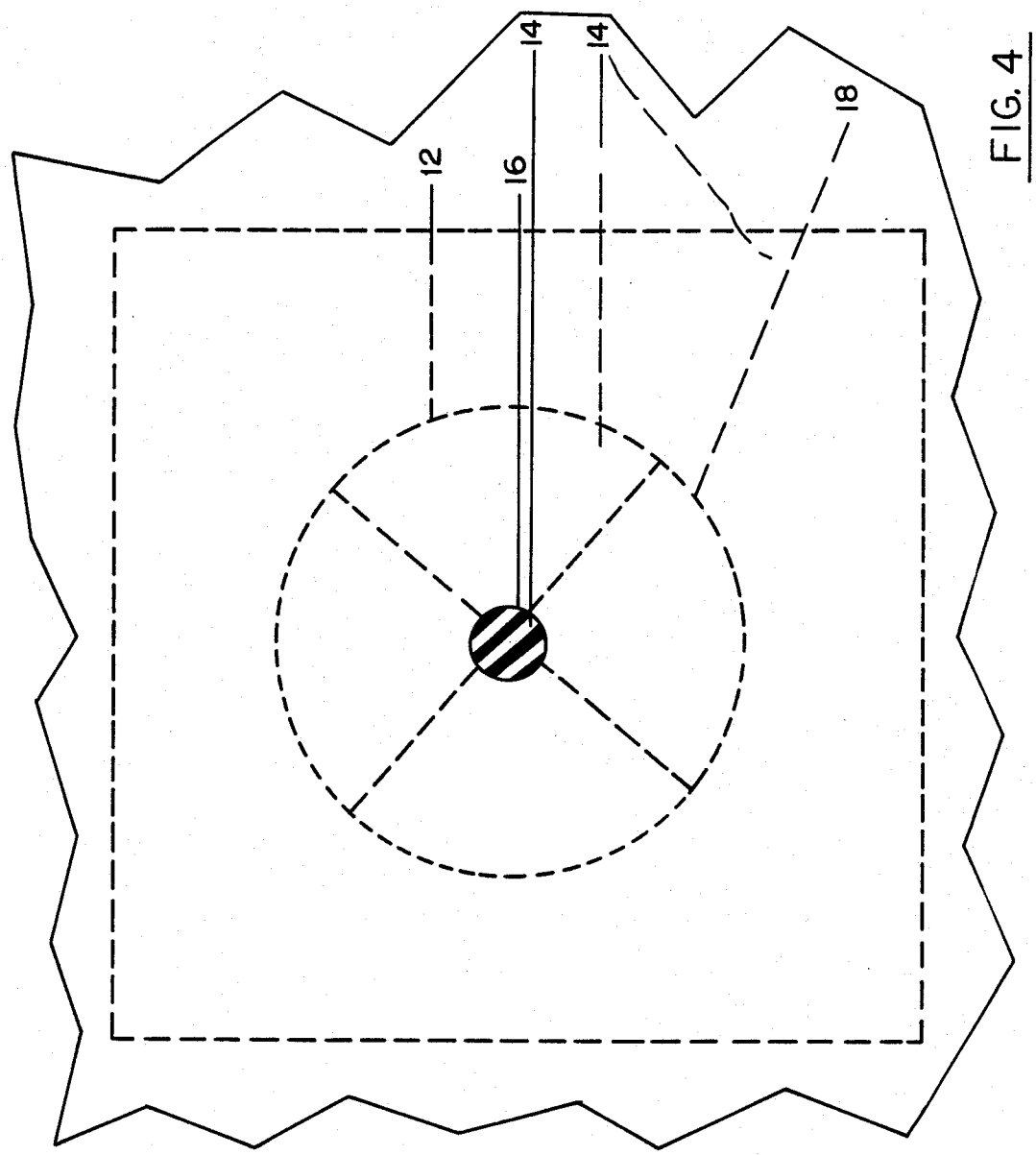
FIG. 4 is a cross-section along the plane of line IV—IV of FIG. 1.

Reference electrode 8 of this invention is capable of reaching stability within a relatively short period of time (e.g., typically less than 20 seconds) due to its unique proportions and size. The ratio of the area of first opening 12 to the area of second opening 16 ranges from about 14.0 to about 728.0. Preferably, this ratio is about 143.3. As can be seen in FIGS. 2 and 4, openings 12 and 16 are circular; however, their circular shapes are not critical. In the preferred embodiment, the area of first opening 12 is about $1.82 \times 10^{-2}$ $cm^2$, and the area of the second opening is about $1.27 \times 10^{-4}$ $cm^2$.

The ratio of distance "d" (i.e., the distance between openings 12 and 16) to the area of first opening 12 ranges from about 2.0 $cm^{-1}$ to about 66.0 $cm^{-1}$. Preferably, this second ratio is about 13.3 $cm^{-1}$.

Cavity 18 can be divided into two zones: reservoir 22 and diffusion chamber 24. Reservoir 22 includes a cylindrical portion 26 which has the diameter of opening 12, and a tapering conical portion 28 which tapers from the diameter of cylindrical portion 26 to the diameter of diffusion chamber 24.

Diffusion chamber 24 is cylindrical, it has the diameter of opening 16. Diffusion chamber 24 has a length ranging from about $1.02 \times 10^{-2}$ to about $1.78 \times 10^{-2}$ cm, preferably $1.27 \times 10^{-2}$ cm. The ratio of the volume of the diffusion chamber to the volume of the rest of the internal cavity (reservoir 22) is about $5.90 \times 10^{-5}$ to about $1.30 \times 10^{-2}$, preferably $5.18 \times 10^{-4}$.

Silver/silver chloride chip 14 preferably comprises a silver-silver chloride matrix layer 30 which is applied to all surfaces of a substrate 32. Substrate 32 can be any inert material such as a plastic or glass. Preferably, substrate 32 is made of a plastic such as acrylonitrile-butadiene-styrene (ABS). The silver-silver chloride matrix layer 30 preferably includes a layer of silver which is deposited directly on substrate 32, and a layer of silver chloride which overlays the silver layer and is exposed directly to electrolyte 20. The silver and the silver chloride layers are applied to chip 32 by conventional electroless plating techniques.

The silver layer is thicker than the silver chloride layer. In the preferred embodiment of this invention, the ratio of the thickness of the silver layer to the thickness of the silver chloride layer is 4 to 1. The exact thicknesses of the two layers depends in large part upon how long the reference electrode is designed to last. The thicknesses also depend on the two layers filling any irregularities in the surface of the substrate. If depressions or peaks in the substrate surface are not filled or covered, a non-homogeneous layer is formed which can reduce the effective surface area of the silver-silver chloride matrix layer. For a single use disposable electrode, the silver layer can be about $1.27 \times 10^{-4}$ cm thick, and the silver chloride layer can be $3.18 \times 10^{-5}$ cm thick. However, a reference electrode of this invention has been constructed which can be used for over 200 separate measurements where the thickness of the silver layer is $2.54 \times 10^{-4}$ cm and the thickness of the silver chloride layer is $6.35 \times 10^{-5}$ cm.

Silver/silver chloride chip 14 is positioned in a recess 34 adjacent opening 12 so that the silver-silver chloride matrix 30 of chip 14 is positioned across opening 12 in direct physical contact with electrolyte 20. Electrical contact to matrix 30 is established from the back side 31 of chip 14 by removing from the back side only the silver chloride layer, leaving the silver layer. The silver chloride layer is removed by exposing it to concentrated ammonium hydroxide. Once the silver chloride layer is removed, an electrical circuit is completed by the attachment of an electrical lead with conductive epoxy to the exposed silver layer of the back side 31 of chip 14.

Electrolyte 20 fills internal cavity 18 completely-including reservoir 22 and diffusion chamber 24. Electrolyte 20 advantageously is a polyacrylamide gel which is impregnated with an alkali metal halide. Polyacrylamide gels can be polymerized externally, according to conventional procedures, and then packed into internal cavity 18 manually. It has been found that when the gel is packed manually into cavity 18, pockets of air can be introduced into the gel. In addition, the amount of polymerized gel can differ between reference electrodes packed manually. The differences in gel amounts lead to differences in impedance between electrodes. Accordingly, polymerizing the gel in place in cavity 18 is preferred. The polyacrylamide gel of electrolyte 20 can be polymerized in place by addition of the polyacrylamide in its monomer form into cavity 18 and exposing the monomer to an appropriate lamp source (e.g. a lamp source such as a Black-Ray lamp or a xenon flash tube).

The advantage of polymerizing the polyacrylamide gel in place is that a precise amount of the relatively non-viscous monomer can be introduced into cavity 18 so that the cavity can be filled without any air pockets. When the monomer is then polymerized to form the gel, the gel conforms to the precise internal dimensions of cavity 18 and will completely fill it without air pockets. The alkali metal halide in the gel should be selected from potassium chloride or sodium chloride. The concentration of the alkali metal halide in the gel ranges from about 0.10 M to about 0.03 M, preferably 0.15 M.

A reference electrode constructed according to the teachings of this invention will have an impedance from about 12 to about 25 kiloohms. This impedance has been found to be lower than the impedance of ion selective electrodes such as the one disclosed in U.S. patent application Ser. No. 56,605 filed June 1, 1987 entitled "Apparatus for Measuring Electrolytes", which application is incorporated herein by reference. Such a reference electrode can be used in tandem with the ion selective electrode in the aforesaid patent application.

Figure 5:
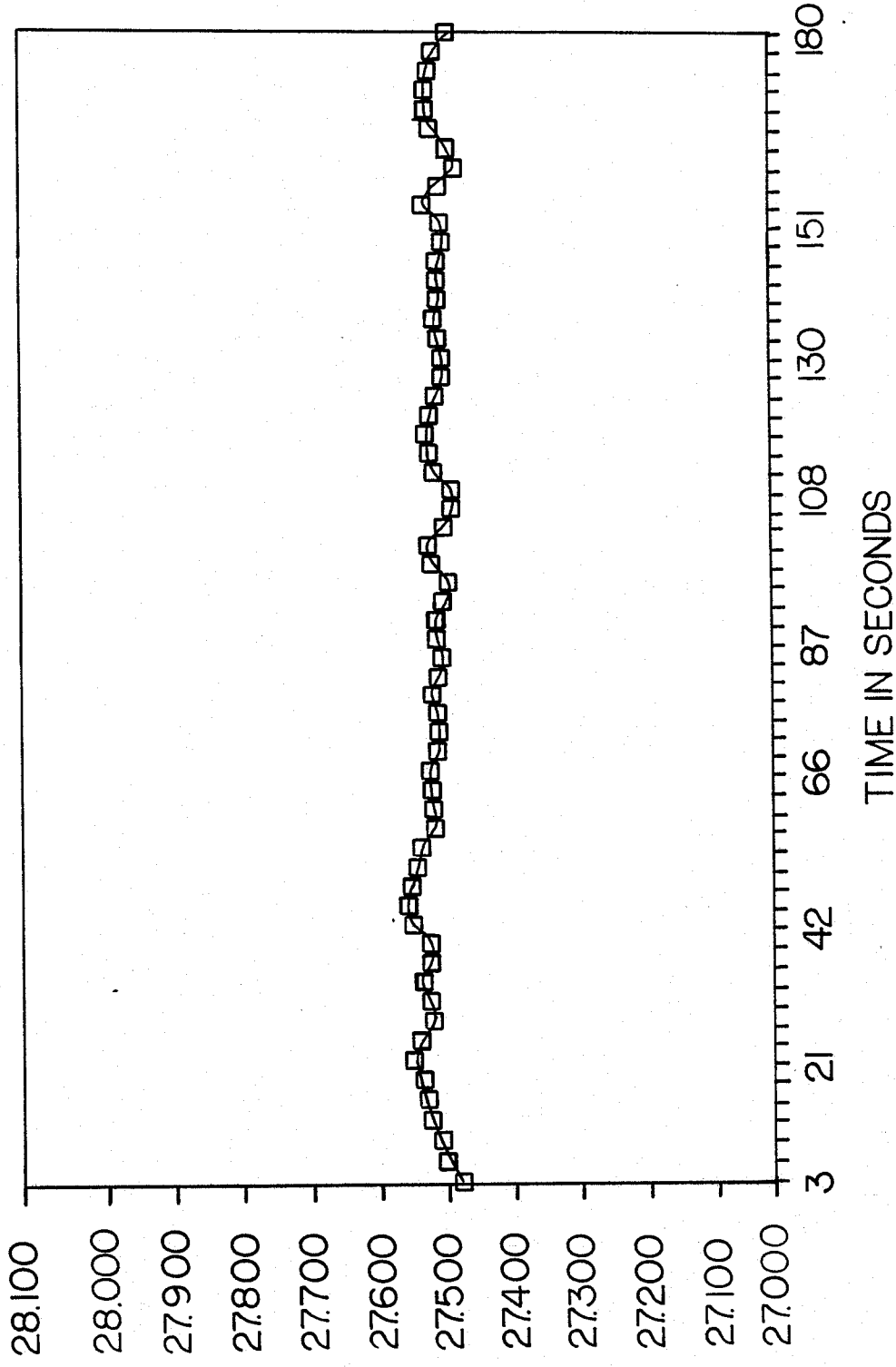
FIG. 5 is a graph illustrating the stability of the reference electrode as compared to its response time.

With such low impedance, the reference electrode of the present invention can stabilize quickly when exposed to a solution containing electrolytes to be measured. The rapidity with which the reference electrode of this invention can reach a stable plateau is illustrated by FIG. 5. The data plotted on FIG. 5 is attained by constructing a test apparatus which includes a thermostated beaker filled with 0.15 M potassium chloride into which three electrodes are placed: the reference electrode of this invention, and two commercially available calomel electrodes (Corning calomel electrode model No. 80062). The two calomel electrodes are preconditioned in the potassium chloride solution for about 20 minutes. The electrolyte inside the reference electrode in this experiment was also 0.15 M potassium chloride.

Initially, the potential between the two calomel electrodes is measured over time, for about three minutes. This acts as a control potential in determining any potential fluctuations as a result of changes within the control solution itself, or any changes due to temperature, pressure and the like. If the potential measured between the two calomel electrodes is relatively constant over the three minute test period, it establishes that the calomel electrodes are working properly.

Once it is established that the calomel electrodes are functioning properly, the stability of the reference electrode can be measured. The stability of the reference electrode is measured against one of the two calomel electrodes. To test the stability of the reference electrode, the reference electrode is not introduced into the testing solution until after the proper functioning of the calomel electrodes is established. Once the reference electrode is introduced into the solution, the potential between the reference electrode and one of the calomel electrodes is monitored continuously. These reference measurements are depicted in FIG. 5 for the first three minutes after the reference electrode is introduced to the solution. While the reference electrode is in the solution, the potential between the two calomel electrodes is also monitored to insure that the calomel electrodes are functioning properly while the reference electrode is in solution. The data in FIG. 5 illustrates that the reference electrode of this invention reaches stability in less than 20 seconds, and maintains that stability for over three minutes. In Applicant's experience, that stability will essentially be maintained for its useful life.

The reference electrode used in the experiment of FIG. 5 had a first opening with an area of $1.82 \times 10^{-2}$ cm$^2$, and a second opening with an area of $1.27 \times 10^{-4}$ cm$^{-2}$. The ratio "d" was 13.3 cm$^{-1}$.

One other advantage of the reference electrode of the present invention that it has a long shelf life between the time it is constructed and the time it is tested. Reference electrodes have been constructed according to the teachings of the present invention which exhibit stability even after three years of storage.

As can be seen by the disclosure above, the reference electrode of the present invention provides an inexpensive electrode which can be constructed to be disposable after one or multiple uses. Furthermore, it can reach a stable condition in a relatively short period of time in contrast to many prior art reference electrodes. The embodiments in which an exclusive property of privileges claimed are defined by the claims which follow.

I claim:

1. A reference electrode, comprising:
   a silver-silver chloride chip; and
   a housing having an internal cavity filled with electrolyte, said cavity having a first opening said chip being disposed to extend across and substantially entirely cover said first opening, and said cavity having a second opening for exposure to a test medium of interest spaced from said first opening; wherein the ratio of the area of the first opening to the area of the second opening is from about 14.0 to about 728.0, and the ratio of the distance between the first and second openings to the area of the first opening is about 2.0 cm$^{-1}$ to about 66.0 cm$^{-1}$.

2. The reference electrode of claim 1 wherein the ratio of the areas of the first and second openings is 143.3.

3. The reference electrode of claim 1 wherein the ratio of said distance and said first opening is 13.3 cm$^{-1}$.

4. The reference electrode of claim 1 wherein the area of said second opening is about $8.00\times10^{-5}$ cm$^2$ to about $3.3\times10^{-4}$ cm$^2$.

5. The reference electrode of claim 4 wherein said second opening area is about $1.27\times10^{-4}$ cm$^2$.

6. The reference electrode of claim 5 wherein said first opening area is about $1.82\times10^{-2}$ cm.

7. The reference electrode of claim 1 wherein said chip comprises an inert substrate having a silver-silver chloride matrix.

8. The reference electrode of claim 7 wherein said silver-silver chloride matrix comprises a layer of silver chloride on a layer of silver, the silver layer being applied to the substrate.

9. The reference electrode of claim 8 wherein the ratio of the thickness of the silver layer to the thickness of the silver chloride layer is 4:1.

10. The reference electrode of claim 1 wherein said electrolyte comprises a polyacrylamide gel impregnated with an alkali metal halide.

11. The reference electrode of claim 10 wherein said alkali metal halide is potassium chloride or sodium chloride.

12. The reference electrode of claim 10 wherein said polyacrylamide is polymerized in said housing.

13. The reference electrode of claim 1 wherein the impedance of the electrode is from about 12 to about 25 kiloohms.

14. The reference electrode of claim 1 further including a diffusion chamber adjacent said second opening, said diffusion chamber being in fluid communication with said internal cavity.

15. The reference electrode of claim 14 wherein the ratio of the volume of said diffusion chamber to the volume of said internal cavity is about $5.90\times10^{-5}$ to about $1.30\times10^{-2}$.

16. The reference electrode of claim 15 wherein said volume ratio is about $5.18\times10^{-4}$.

* * * * *